United States Patent [19]
Manwaring

[11] Patent Number: 5,122,138
[45] Date of Patent: Jun. 16, 1992

[54] TISSUE VAPORIZING ACCESSORY AND METHOD FOR AN ENDOSCOPE

[76] Inventor: Kim H. Manwaring, 3703 E. Nambe Ct., Ahwatukee, Phoenix, Ariz. 85044

[21] Appl. No.: 619,224

[22] Filed: Nov. 28, 1990

[51] Int. Cl.$^5$ ............................................. A61B 17/39
[52] U.S. Cl. ..................................... 606/46; 606/49
[58] Field of Search ................................. 606/27–31, 606/46, 45, 49, 41, 42

[56] References Cited

U.S. PATENT DOCUMENTS

| | | | |
|---|---|---|---|
| 2,275,167 | 3/1942 | Bierman | 606/49 |
| 4,807,620 | 2/1989 | Strul et al. | 606/28 |
| 4,927,420 | 5/1990 | Newkirk et al. | 606/45 |
| 4,936,301 | 6/1990 | Rexroth et al. | 606/45 |
| 4,943,290 | 7/1990 | Rexroth et al. | 606/45 |

FOREIGN PATENT DOCUMENTS

WO86/05379 9/1986 World Int. Prop. O. ............ 606/45

*Primary Examiner*—Lee S. Cohen
*Assistant Examiner*—J. R. Jastrzab
*Attorney, Agent, or Firm*—Cahill, Sutton & Thomas

[57] ABSTRACT

A flexible tube having first and second ends and a hollow interior is insertable through an endoscopic instrument channel with the first end extending out of the viewing end of the endoscope and the second end extending out of the working end of the endoscope a sufficient distance to lie within the field of view of the endoscope observation port. The second end of the flexible tube defines a tube end face. A flexible electrical conductor having an outer surface sized to fit within the interior of the flexible tube and to define a gap between the conductor outer surface and the interior surface of the tube includes first and second ends. The first end of the conductor extends out of the endoscope viewing end while the second end is located within a recessed chamber extending between the tube end face and a spaced apart location within the interior of the tube to define a high impedance gap between the second end of the conductor and a nearby region including the tube end face and an adjacent tissue. A monopolar RF generator is coupled to the first end of the electrical conductor for periodically transmitting a defined RF output signal along the conductor to cause current to jump across the high impedance gap to thereby generate a high temperature zone in proximity to the gap. Appropriate manipulation of the endoscope working end to position the tube end face in proximity to the tissue achieves controlled heating and vaporization of the tissue.

26 Claims, 2 Drawing Sheets

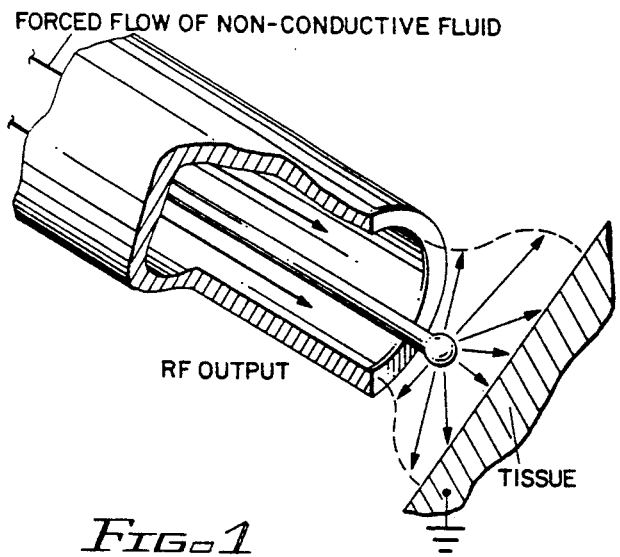
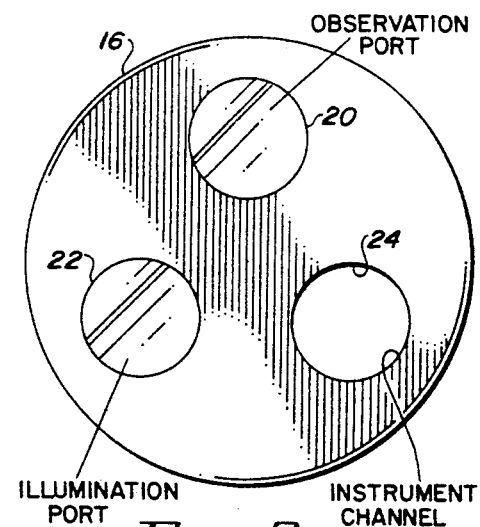
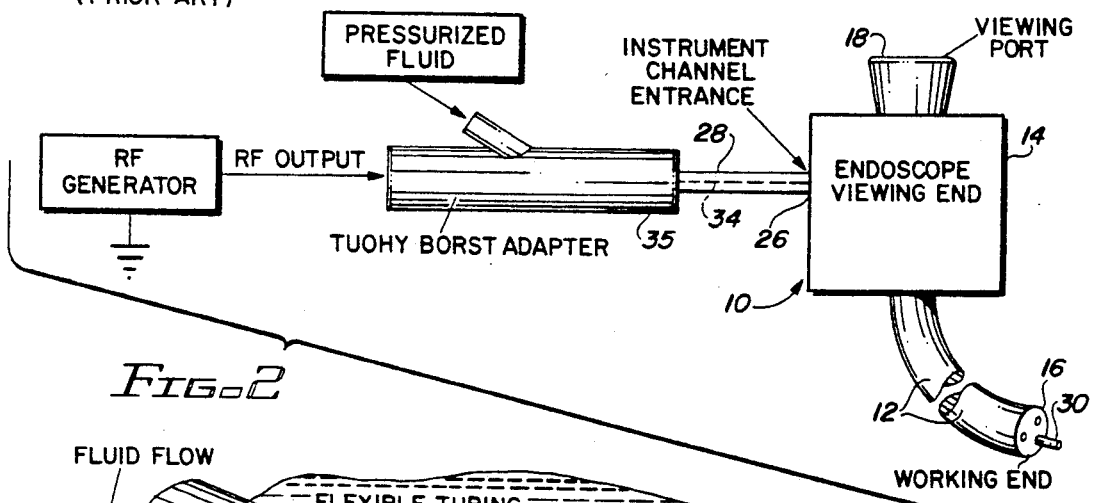
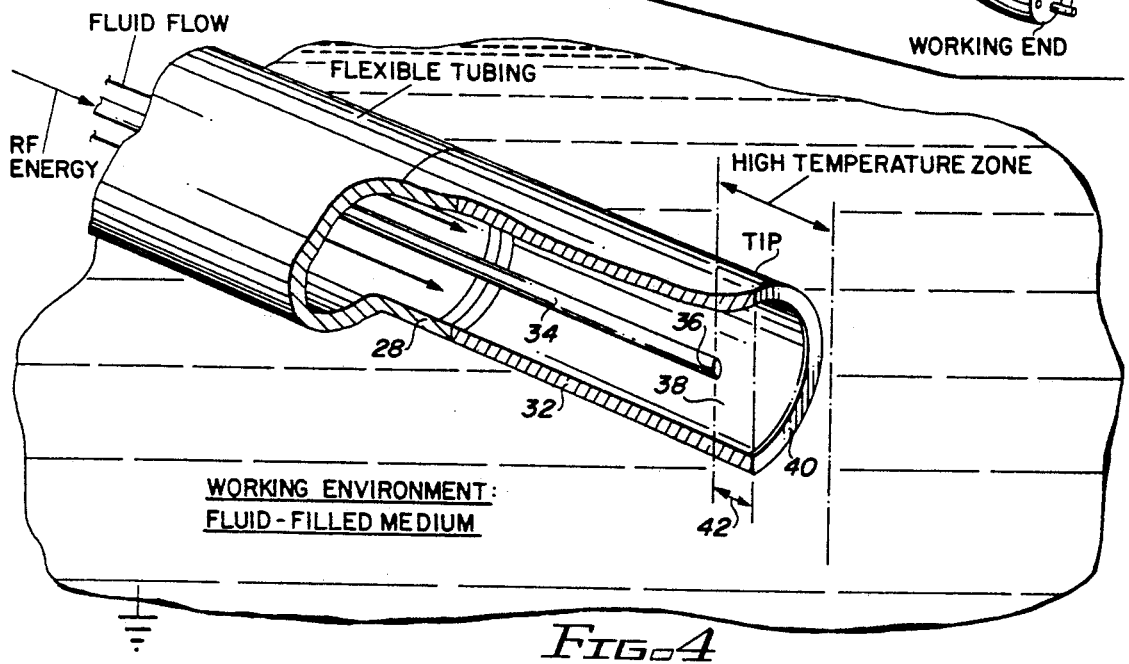

TISSUE VAPORIZING ACCESSORY AND METHOD FOR AN ENDOSCOPE

BACKGROUND OF THE INVENTION

1. Field of the Invention

This invention relates to endoscopic surgical devices, and more particularly, to radio frequency energized endoscopic tissue dissection and coagulation devices.

2. Description of the Prior Art

U.S. Pat. No. 4,943,290 (Rexroth) discloses an electrolyte purging electrode tip suitable for use in an arthroscopic surgical system. In arthroscopic surgery, dissection or tissue cutting must take place within a joint cavity which is normally filled with an electrically conductive fluid including, for example, a local anaesthetic administered in a sodium chloride diluent or blood which also includes an electrically conductive sodium chloride diluent.

The presence of such electrically conductive fluids in the presence of the electrode tip causes unacceptably severe dissipation of electrical energy at the tip of the cutting electrode, requiring substantially increased levels of RF energy. In seeking to overcome unwanted RF power dissipation caused by operation of the RF-energized electrode cutting tip in an electrically conductive medium, higher RF power levels are required, but result in reduced cutting accuracy, significantly increased tissue heating and tissue smoking.

To solve this problem, Rexroth invented a system schematically illustrated in FIG. 1 (Prior Art) which injects a flow of non-conductive fluid (E.G. distilled water) out the end of a flexible tube to thereby surround the tip of the RF electrode with the electrically non-conductive fluid. By eliminating electrically conductive fluid from the substantially spherical region surrounding the exposed electrode tip, Rexroth avoids unwanted dissipation of RF energy and the heating power of the RF electrode is more easily concentrated on the tissue to be dissected or coagulated.

While the electrolyte purging electrode tip taught by Rexroth is quite acceptable for arthroscopic surgery, such techniques are unacceptable for other types of surgery. For example, the Rexroth electrolyte purging electrode tip system cannot be used for electrosurgery in the human brain which is surrounded by a fluid-filled medium in the form of cerebrospinal fluid (CSF). CSF represents a relatively highly conductive electrolyte which, if disturbed by the injection of a non-conductive electrolyte such as distilled or non-ionized water or the equivalent as taught by Rexroth, leads to unacceptable and potentially dangerous swelling of the brain tissue. The Rexroth system which requires the injection of a non-conductive fluid into the CSF electrolyte has therefore been unacceptable for neurosurgical applications.

For neurosurgical applications, tissue dissection is presently accomplished by mechanical biting or cutting devices or by laser heating devices which can also accomplish tissue coagulation. The biting and cutting devices as well as the laser device are packaged in relatively large diameter tubular bundles and require that a relatively large entrance aperture be bored into the human skull. Both the biting and cutting devices as well as the laser devices are also relatively inflexible and are therefore difficult to maneuver within the interior of the human brain. Because of the high level of sophistication of laser-energized tissue dissection and coagulation devices, laser systems typically cost on the order of about fifty thousand dollars.

SUMMARY OF THE INVENTION

It is therefore a primary object of the present invention to provide a tissue vaporizing accessory for an endoscope which is highly flexible, small in diameter, simple in construction and low in cost, yet which can utilize radio frequency energy from a monopolar RF generator to either cut, coagulate or vaporize tissue located within a fluid-filled medium having either electrically conductive or non-electrically conductive characteristics.

Another object of the present invention is to provide a tissue vaporizing accessory for an endoscope which can create an intense, high temperature zone at a controlled location while emitting only relative low power levels in proximity to the surgical site.

Yet another object of the present invention is to provide a tissue vaporizing accessory for an endoscope which can accomplish vapor purging, debris clearance and other irrigation functions by injecting an electrically conductive fluid into the operating zone where the electrical conductivity characteristics of the fluid may be closely matched to the electrical conductivity characteristics of cerebrospinal fluid.

Still another object of the present invention is to provide a tissue vaporizing accessory for an endoscope which can be coupled to and energized by a generic monopolar RF generator typically available at virtually all surgically equipped hospital facilities.

Briefly stated, and in accord with one embodiment of the invention, a tissue vaporizing accessory is provided for an endoscope which includes a flexible, tubular body having a viewing end and a working end insertable into a fluid-filled medium. The endoscope further includes a viewing channel having an observation port for transmitting an image of a defined field of view around the working end of the endoscope to a viewing port positioned at the viewing end of the endoscope. An illumination port is positioned at the working end of the endoscope for illuminating the defined field of view around the observation port. A hollow instrument channel extends from the viewing end to the working end of the endoscope. The tissue vaporizing accessory for the endoscope comprises a flexible tube having first and second ends and a hollow interior with an interior surface. The tube is insertable through the endoscope instrument channel with the first end extending out of the viewing end of the endoscope and with the second end extending out of the working end of the endoscope a sufficient distance to lie within the defined field of view of the observation port. The second end of the flexible tube further defines an end face of the tube. A flexible electrical conductor having an outer surface sized to fit within the interior of the flexible tube and to define a gap between the conductor outer surface and the interior surface of the tube further includes a first end extending out of the endoscope viewing end and a second end. The second end of the flexible electrical conductor is located within a recessed chamber extending between the tube end face and a spaced apart location within the interior of the tube to define a high impedance gap between the second end of the conductor and a nearby region including the tube end face as well as an adjacent tissue. A monopolar RF generator is coupled to the first end of the electrical conductor for periodically transmitting a defined RF output signal along the conductor to cause current to jump across the high impedance gap to thereby generate a high temperature zone in proximity to the gap. Appropriate manipulation of endoscope working end to position the tube end face in proximity to the tissue achieves controlled heating and vaporization of the tissue.

DESCRIPTION OF THE DRAWINGS

The invention is pointed out with particularity in the appended claims. However, other objects and advantages together with the operation of the invention may be better understood by reference to the following detailed description taken in connection with the following illustrations, wherein:

FIG. 1 represents a simplified depiction of an element of the prior art electrolyte purging electrode tip disclosed in U.S. Pat. No. 4,943,290 to Rexroth.

FIG. 2 represents a schematic block diagram symbolically depicting the various elements which function together in an endoscopic surgical system including the tissue vaporizing accessory of the present invention.

FIG. 3 represents a simplified end view of the working end of the endoscope illustrated in FIG. 2.

FIG. 4 represents a partially cutaway sectional view depicting the second end of the flexible tube of the tissue vaporizing accessory and the second end of the flexible electrical conductor.

DESCRIPTION OF THE PREFERRED EMBODIMENT

Figure 5:
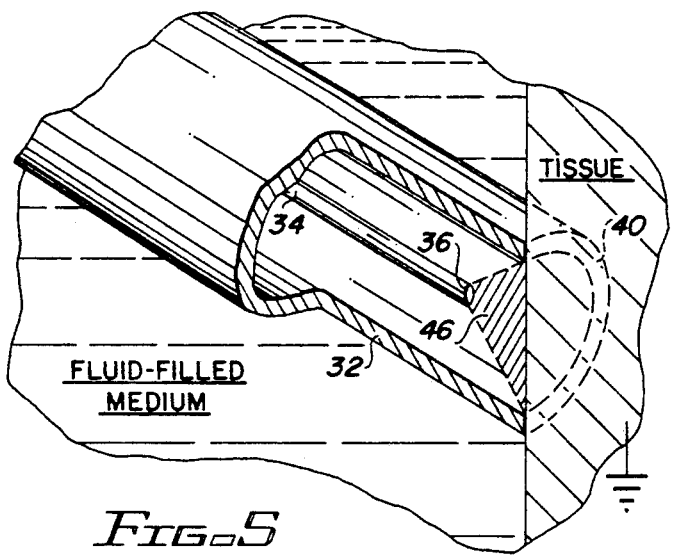
FIG. 5 represents a partially cutaway sectional view of the end section of the tissue vaporizing accessory of the present invention illustrated in the manner in which the invention focusses or concentrates RF energy from a monopolar RF generator and creates a high temperature zone which can be positioned in proximity to a tissue immersed in a fluid-filled medium.

In order to better illustrate the advantages of the invention and its contributions to the art, a preferred hardware embodiment of the invention will now be described in some detail.

Referring now to FIGS. 2 and 3, a miniaturized endoscope, also known as a ventriculoscope in neurosurgical applications, is schematically illustrated in FIG. 2. Endoscope 10 includes a tubular body 12 having a viewing end 14 and a working end 16 which can be inserted into a fluid-filled medium such as cerebrospinal fluid (CSF) which surrounds brain tissue.

An endoscope of the type schematically depicted in FIG. 2 also includes a fiberoptic viewing channel (not shown) which extends along the entire length of the endoscope and includes a first end coupled to a viewing port 18 and a second end port coupled to observation port 20. The viewing channel is designed to transmit an image of a defined field of view around the working end 16 to viewing port 18.

Endoscope 10 further includes a illumination port 22 located in the endoscope working end 16 for illuminating the defined field of view around observation port 20.

A hollow instrument channel, the end of which is depicted in FIG. 3 and designated by reference number 24, extends from instrument channel entrance port 26 located in endoscope viewing end 14 along the length of tubular body 12 to the location illustrated in FIGS. 2 and 3 where the instrument channel terminates in the working end 16 of the endoscope.

One preferred embodiment of an endoscope suitable for neurological applications is commercially available from Codman & Shutteff, Inc. of Randolph, Mass. and is generally designated as a flexible, steerable fiberoptic ventriculoscope.

Referring now to FIGS. 2, 3 and 4, the tissue vaporizing accessory for endoscope 10 will now be described in detail.

A flexible tube 28 includes a first end (not specifically illustrated) which extends within and is coupled to a coupling device or adapter which in the preferred embodiment takes the form of a commercially available Tuohy-Borst adapter. The body of flexible tube 28 extends through instrument channel entrance 26 of endoscope 10 and through the full length of the endoscope instrument channel along tubular body 12 and is positioned lengthwise relative to the instrument channel such that a second end 30 extends out of the working end 16 of endoscope 10 a sufficient distance to lie within the defined field of view of observation port 20.

In the embodiment of the invention illustrated in FIGS. 2, 3 and 4, the flexible tube can take the form of a commercially available nineteen gauge Teflon epidural catheter commercially available from a number of sources including the Deseret Company of Sandy, Utah. The outer diameter of this plastic or Teflon, electrically non-conductive or insulating tube is dimensioned to approximate the one millimeter internal diameter of the endoscope instrument channel 24. The wall of flexible tube 28 must possess a flexibility compatible with the flexibility of tubular body 12 of endoscope 10. Teflon catheters of the type identified above have been found highly suitable for use in connection with the tissue vaporizing accessory of the present invention.

Figure 6:
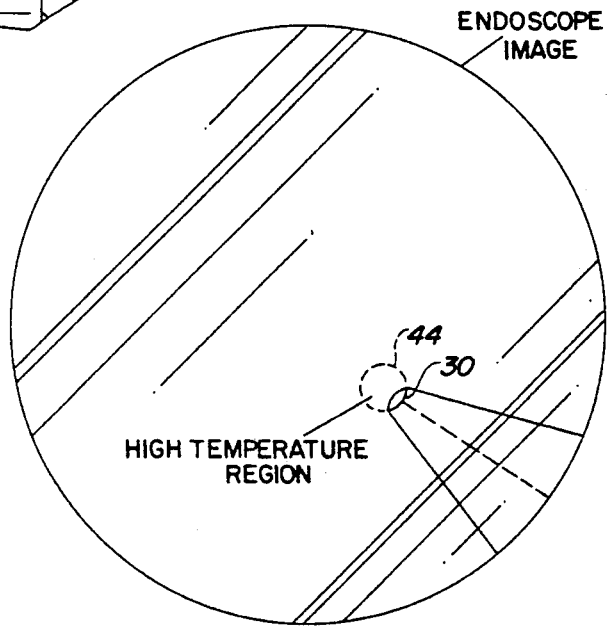
FIG. 6 represents a simplified diagram of an endoscopic image as seen by a neurosurgeon using the tissue vaporizing accessory for an endoscope of the present invention.

The length that second end 30 of flexible tube 28 extends beyond the working end 14 of endoscope 10 is readily adjusted by the surgeon as illustrated in FIG. 6. During this adjustment procedure, the surgeon looks through endoscope viewing port 18 and adjusts the relative position of the second end of flexible tube 28 by gripping flexible tube 28 in proximity to the instrument channel entrance 26 and either extending or retracting the two until second end 30 lies within the defined field of view provided by endoscope observation port 20 and the endoscope viewing channel. FIG. 6 represents one suitable position for second end 30 of flexible tube 28 although the position of second end 30 can be relocated to any other suitable location within the defined field of view surrounding the working end 16 of the endoscope. Such a position permits a neurosurgeon to first locate the tissue to be operated on and then, second, to observe in real time the actual heating, cutting, coagulating and/or vaporizing being accomplished by the tissue vaporizing accessory of the present invention.

Although the tissue vaporizing accessory can work for a limited time by permitting the end of the Teflon catheter itself to function as the second end 30 of flexible tube 28, longer life and overall improved performance is achieved when, as illustrated in FIG. 4, a special high temperature tip 32 having dimensions compatible with tube 28 is coupled to tube 28 as illustrated in FIG. 4. The length of high temperature tip is not particularly critical and can be adjusted as requirements dictate. Because the preferred refractory materials such as glass or ceramic are rigid, it is desirable to minimize the overall length of tip 32. On the other hand, the length of tip 32 must not be shortened to such a degree that the high temperature zone created by the tissue vaporizing accessory of the present invention causes melting or distortion of the abutting end of the non-refractory, flexible tube 28 which after a reasonably short period of time will be melted or distorted by the high temperatures generated by the tissue vaporizing accessory. In the preferred embodiment of the invention, the length of high temperature tip 32 has been selected to equal approximately five millimeters.

A flexible electrical conductor 34 (stainless steel wire or high temperature resistant tungsten wire) includes an outer surface or diameter sized to fit within the interior of flexible tube 28. In the preferred embodiment of the invention, flexible tube 28 includes an outer diameter on the order of about one millimeter and an inner diameter on the order of about two thirds of a millimeter. It is not necessary to provide insulation on electrical conductor 34. It has been found that even when commercially available Teflon catheters including a spiral wound steel reinforcing spring are used, it is not necessary to avoid electrical contact between the spring and electrical conductor 34. In addition, electrical conductor 34 can either be configured as a single conductor wire or as a multiple conductor such as, for example a three conductor stranded wire, and will function suitably in combination with the present invention.

The first end (not shown) of electrical conductor 34 extends coaxially through tube 28, out of instrument channel entrance 26 and into the interior of the Tuohy-Borst adaptor 35 where it is coupled to the RF output of a commercially available monopolar radio frequency (RF) generator. The second end 36 of conductor 34 is located within a recessed cylindrical chamber 38 which has a first surface location defined by the second end 36 of conductor 34 and a second surface defined by the end face 40 of either flexible tube 28 if no high temperature tip 32 is provided or by the end of tip 32 as illustrated in FIG. 4 and designated by reference number 40. In the configuration of the invention illustrated in FIG. 4 where both flexible tube 28 and high temperature tip 32 possess a cylindrical cross section, end face 40 is configured as a circular surface. This circular surface defines the cutting pattern for the tissue vaporizing accessory as will be explained below.

For the specific dimensions of tube 28, tip 32 and electrical conductor 34 stated above, it has been experimentally determined that the depth of recessed chamber 38 as designated by reference number 42 in FIG. 4 can vary from approximately two millimeters to zero where second end 36 of conductor 34 virtually contacts but does not penetrate beyond end face 40. For different tube diameters, different electrical conductor diameters, different materials or different RF generator power levels and frequencies and other combinations and permutations of the structure disclosed, it may be possible to achieve proper operation of the present invention where the depth 42 of recessed chamber 38 exceeds two millimeters. Such a determination could readily be made by one of ordinary skill in the art following the teachings of this invention.

Referring now to FIGS. 4 and 5, the distance between conductor tip second end 36 and end face 40 defines a high impedance gap which by appropriate manipulation of the endoscope working end 16 into a position near the tissue to be operated upon also brings the high impedance gap into proximity of the tissue. Such positioning is readily observed by the operating neurosurgeon as illustrated in FIG. 6. When the appropriate position of end face 40 of the tissue vaporizing accessory has been achieved as illustrated in FIGS. 5 and 6, the neurosurgeon actuates the RF generator for varying periods of time, typically in a repetitive series of "on" pulses of from one tenth of a second to as long as one second, to create a high temperature region as illustrated in FIG. 6 and designated by reference number 44.

The size, temperature level and cutting effect of the tissue vaporizing attachment can be controlled by the neurosurgeon by controlling the RF generator output period wave form configuration, pulse duration and relative proximity between end face 40 and an adjacent tissue.

For typical commercially available monopolar RF generators such as a Force 4B generator available from Valleylab, Inc. of Boulder, Colo., the RF generator output power can be adjusted, the output frequency can be varied and the output wave form can be varied. For typical operation of the tissue vaporizing accessory of the present invention in neurosurgical applications in cerebrospinal fluid, power levels are normally selected to be on the order of about thirty watts. Although the RF generator output frequency can be varied between four hundred kiloHertz to eight hundred kiloHertz, optimum performance has been achieved with an RF generator output frequency on the order of about five hundred kiloHertz. In accordance with standard practice, the RF generator is grounded to the patient on whom surgery is to be performed.

The output wave form of the RF generator can be varied as required by the specific surgical application. For cutting applications, a continuous sine wave output may be selected. For coagulation applications, a damped sine wave output may be selected with a pulsed output having a thirty thousand Hertz pulse repetition rate. Various other wave forms and pulse repetition rates could readily be provided and selected by those of ordinary skill in the art.

In operation, as best illustrated in FIG. 5, actuation of the RF generator creates a strong electric field 46 between conductor tip 34 and end face 40 which results in near instantaneous sparking within region 46. When end face 40 is placed either in close proximity to or in contact with a tissue as illustrated in FIG. 5, the sparking results in the generation of extremely high temperatures causing vaporization of the fluid within region 46 and virtually instantly achieves temperatures estimated to reach approximately four hundred degrees Centigrade. The adjacent tissue is rapidly desiccated and then vaporized. Such RF sparking followed by fluid vaporization is generally referred to as fulguration and is a well known phenomenon.

As illustrated in FIGS. 2 and 4, a source of pressurized fluid such as electrically conductive saline can be injected into the second input of Tuohy-Borst adaptor 35 to provide a controlled, relatively slow flow of fluid through the length of tube 28 and out end face 40 of the tissue vaporizing accessory. In neurosurgical applications in cerebrospinal fluid, the injection of saline into the cerebrospinal fluid does not create any adverse effects including tissue swelling since the electrical conductivity of saline is highly compatible with the electrical conductivity of the cerebrospinal fluid. Typically, 0.9 normal saline (155 mEq sodium chloride per 1000 ML) works very satisfactorily. The flow of saline into the cerebrospinal fluid is typically controlled to be continuous at about three to four drops per second.

Although not required for proper function or operation of the tissue vaporizing accessory, the flow of an irrigating fluid out of end face 40 of the tissue vaporizing accessory enhances the overall operation of the invention by purging or clearing vapor (steam bubbles) from the defined field of view of the endoscope viewing channel and from the heated surface of the tissue and also clears debris resulting from the tissue vaporizing function of the invention. If the source of pressurized fluid as illustrated in FIG. 2 were omitted, some alternative means would have to be provided to fill at least the interior of tip 32 with a fluid to enable the invention to operate in the fulguration mode as described above while sparking between conductor tip 36 and end face 40 creates extremely high temperature steam and heat. In such an alternative embodiment of the invention, a neutral or negative pressure could be provided within the hollow interior of tube 28 such that fluid from the fluid-filled medium of the working environment could be sucked into or drawn up tube 28 to a sufficient elevation.

As illustrated in FIG. 5, the unique placement of conductor tip 36 within recessed chamber 38 provides a focussing or collimating effect on the RF output from conductor tip 36 as illustrated by shaded region 46. This focussing or concentrating of the RF energy from the RF generator eliminates the necessity to provide a flow of non-electrically conductive (insulating) fluid as disclosed in U.S. Pat. No. 4,943,290 to Rexroth where the flow of such fluid was required to prevent unacceptable dispersion and dissipation of the RF output from the exposed tip of his arthroscopic surgery electrode.

The unique recessed placement of conductor end 36 within a shielded chamber defined by either the end section of a plastic tubular member 28 or the end section of a refractory tip 32 provides a completely different structure or means for eliminating the RF dispersion dealt with in a completely different manner by Rexroth. As a result, the tissue vaporizing accessory of the present invention can utilize either electrically conductive or electrically non-conductive fluid, depending on requirements dictated by particular surgical applications. For neurosurgical applications within an electrically conductive fluid such as cerebrospinal fluid, it is essential that an electrically conductive fluid such as saline be used to prevent swelling of the brain tissue.

Figure 7A:
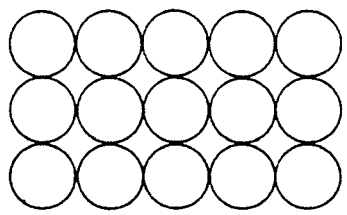
FIGS. 7A-7C depict variations in the cutting patterns which can be implemented by the present invention to remove a section of tissue (FIG. 7A), to cut a line in tissue using a circular end face on the tissue vaporizing accessory (FIG. 7B) or to cut a line in tissue using an elliptical end face on the tissue vaporizing accessory (FIG. 7C).
Figure 7B:
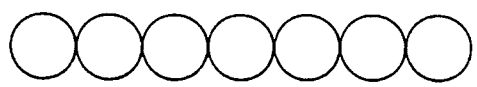
Figure 7C:
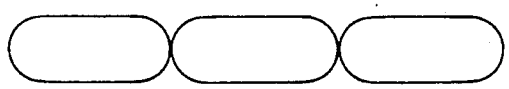

Referring now to FIGS. 7A-7C, another unique aspect of the present invention will now be described. Because as illustrated in FIGS. 5 and 6, high temperature steam is generated at and exits from end face 40, the configuration of end face 40 defines and controls the geometry of the tissue which is heated and vaporized. For a cylindrical tip 32 having a cylindrical end face as illustrated in FIGS. 5 and 6, a single circular cut or vaporized region will appear in the tissue as illustrated in FIG. 7A for each discrete activation of the RF generator. The pulse length of each activation is controlled by the operator or neurosurgeon and typically will last from approximately one tenth to about one second, although longer or shorter activation times could be readily implemented.

As illustrated in FIG. 7A, for each discrete activation of RF generator, a discrete cylindrical cutout or cookie cut is created. To remove or cut a selected substantially rectangular area of the tissue, this series of circular cookie cuts are positioned into the desired rectangular pattern as shown in FIG. 7A.

To make a more linear cut as illustrated in FIG. 7B, the working end 16 of the endoscope is manipulated to place the series of circular cookie cuts side to side to create either a straight or curved line as appropriate.

As illustrated in FIG. 7C, the configuration of end face 40 could be modified into any one of a well known variety of geometric patterns including an ellipse which would provide more elongated cookie cuts into adjacent tissue.

Although as illustrated in FIG. 5, the end face 40 of the tissue vaporizing accessory has been illustrated as either being positioned in contact with or in close proximity to (within about less than 2 millimeters from the tissue), to achieve the results illustrated in FIG. 7, the present invention will operate equally well in the fluid filled medium when spaced well apart from the tissue. The present invention will function to create an intense region of heat at any location within the fluid-filled medium, whether adjacent to or spaced apart from the tissue itself. Such a local heating effect can be useful in the gentle shrinkage of a cyst wall or a vascular tissue within the brain such as choroid plexus.

In order to define the limits of the present invention, the second end 36 or tip of electric conductor 34 was repositioned to penetrate outside of or beyond the end face 40. It was discovered that the tissue vaporizing accessory would not work in an acceptable manner when the recessed chamber was eliminated by causing end 36 of electrical conductor 34 to penetrate through end face 40 toward the tissue. The maximum depth of recessed chamber 38 for the materials and dimensions recited above has been found to be on the order of two millimeters although further investigation with dimensions and different materials could readily be undertaken by one of ordinary skill in the art to potentially expand the depth of recessed chamber 38 beyond two millimeters.

One substantial advantage of the present invention is that it works with a standard RF generator and a standard endoscope typically available for use by surgeons. The flexible tube, flexible electrical conductor and refractory tip (if used) elements of the tissue vaporizing accessory can be acquired for no more than a few dollars. The results achieved by this exceedingly low cost device are comparable to, if not superior to, the results achieved by a $50,000 laser tissue vaporizing system; the flexibility of the tubular body of the present endoscopic system substantially exceeds the flexibility of the laser system; and the diameter of the working end and tubular body of the present invention is also significantly less than the corresponding diameter of the laser system.

It will apparent to those skilled in the art that the disclosed tissue vaporizing accessory for an endoscope may be modified in numerous other ways and may assume many embodiments other than the preferred forms specifically set out and described above. For example, any one of a wide variety of flexible tubes could be substituted for the flexible tube 28 including either electrically conductive or electrically insulating tubes. In addition, the rate of flow of pressurized fluid can be varied from a relatively low level to a higher level, but at higher fluid flow rates, the RF generator power output must be increased since the volume of fluid which must be maintained in the heated state is increased by increased fluid flow rates. Accordingly, it is intended by the appended claims to cover all such modifications of the invention which fall within the true spirit and scope of the invention.

I claim:

1. A tissue vaporizing accessory for an endoscope, the endoscope having a flexible, tubular body with a viewing end and a working end insertable into a fluid-filled medium and further including
   i. a viewing channel having an observation port for transmitting an image of a defined field of view around the working end of the endoscope to a viewing port positioned at the viewing end of the endoscope;
   ii. an illumination port positioned at the working end of the endoscope for illuminating the defined field of view around the observation port;
   iii. a hollow instrument channel extending from the viewing end to the working end of the endoscope; the tissue vaporizing accessory comprising:
   a. a flexible tube having first and second ends and a hollow interior with an interior surface, the tube being insertable through the endoscope instrument channel with the first end extending out of the viewing end of the endoscope and the second end extending out of the working end of the endoscope a sufficient distance to lie within the defined field of view of the observation port, the second end further defining an end face of the tube;
   b. a flexible electrical conductor having an outer surface sized to fit within the interior of the flexible tube and to define a gap between the conductor outer surface and the interior surface of the tube, the conductor further including a first end for extending out of the endoscope viewing end and a second end located within a recessed chamber extending between the tube end face and a spaced apart location within the interior of the tube to define a high impedance gap between the second end of the conductor and a nearby region including the tube end face and an adjacent tissue; and
   c. a monopolar RF generator coupled to the first end of the electrical conductor for periodically transmitting a defined RF output signal along the conductor to cause current to jump across the high impedance gap to thereby generate a high temperature zone in proximity to the gap,
   whereby appropriate manipulation of the endoscope working end to position the tube end face in proximity to the tissue achieves controlled heating and vaporization of the tissue.

2. The tissue vaporizing accessory of claim 1 further including a source of fluid and an adapter coupled to the first end of the flexible tube and to said source of fluid for injecting fluid through the tube and out the end face of the tube.

3. The tissue vaporizing accessory of claim 2 wherein the adapter includes a Tuohy-Borst adaptor.

4. The tissue vaporizing accessory of claim 2 wherein the flexible tube includes a plastic catheter.

5. The tissue vaporizing accessory of claims 2 or 4 further including a tip fabricated from a refractory material coupled to the second end of the flexible tube and the end face forms a part of the tip.

6. The tissue vaporizing accessory of claim 2 wherein the source of fluid includes a source of electrically conductive fluid.

7. The tissue vaporizing accessory of claim 2 wherein the source of fluid includes a source of electrically nonconductive fluid.

8. The tissue vaporizing accessory of claim 1 wherein the second end of the electrical conductor is spaced apart from the end face of the tube toward the first end of the tube by a distance of approximately two millimeters or less.

9. The tissue vaporizing accessory of claim 1 wherein the flexible tube includes a length adequate to enable the second end of the flexible tube to penetrate beyond the working end of the endoscope by a distance exceeding two millimeters.

10. The tissue vaporizing accessory of claim 1 wherein the second end of the flexible tube includes a tip fabricated from an electrical insulating material.

11. The tissue vaporizing accessory of claim 10 wherein the tip is fabricated from a refractory material.

12. The tissue vaporizing accessory of claim 11 wherein the tip is cylindrical in configuration.

13. The tissue vaporizing accessory of claim 12 wherein the tip includes a circular end face and wherein the high temperature zone generated in proximity to the high impedance gap includes a substantially circular cross section.

14. The tissue vaporizing accessory of claim 13 wherein the recessed chamber is formed within the cylindrical tip and wherein the cylindrical tip channels the RF output signal from the RF generator through the fluid-filled medium to the tissue.

15. A method for vaporizing a tissue including the steps of:
   a. providing an endoscope including a flexible, tubular body having a viewing end and a working end, a viewing channel having an observation port for transmitting an image of a defined field of view around the working end of the endoscope to a viewing port positioned at the viewing end of the endoscope, an illumination port positioned at the working end of the endoscope for illuminating the defined field of view around the observation port, and a hollow instrument channel extending from the viewing end to the working end of the endoscope;
   b. inserting the working end of the endoscope into a fluid-filled medium including a tissue;
   c. inserting a flexible tube having first and second ends and a hollow interior with an interior surface through the endoscope instrument channel with the first end extending out of the viewing end of the endoscope and the second end extending out of the working end of the endoscope a sufficient distance to lie within the defined field of view of the observation port, the second end further defining an end face of the tube;
   d. selecting an electrical conductor having an outer surface sized to fit within the interior of the flexible tube to define a gap between the conductor outer surface and the interior surface of the tube, the conductor including first and second ends;
   e. displacing the electrical conductor through the hollow interior of the tube such that the first end extends out of the endoscope viewing end and the second end terminates within a recessed chamber extending between the tube end face and a spaced apart location within the interior of the tube to define a high impedance gap between the second end of the conductor and a nearby region including the tube end face and an adjacent area of the tissue;

f. coupling a monopolar RF generator to the first end of the electrical conductor and periodically actuating the RF generator to transmit a defined RF output signal along the conductor to cause current to jump across the high impedance gap to thereby generate a high temperature zone in proximity to the gap while simultaneously manipulating the endoscope working end to position the tube end face in proximity to the tissue to achieve controlled heating and vaporization of the adjacent area of the tissue.

16. The method of claim 15 including the further step of providing a refractory tip for the second end of the flexible tube.

17. The method of claim 15 including the further step of coupling the first end of the flexible tube to a source of fluid and injecting fluid through the tube and out the second end of the tube.

18. The method of claim 17 including the further step of injecting an electrically conductive fluid through the tube and out the second end of the tube.

19. The method of claim 17 including the further step of injecting an electrically non-conductive fluid through the tube and out the second end of the tube.

20. The method of claim 17 wherein the fluid is passed through the flexible tube and out the second end of the tube to purge bubbles from the recessed chamber and to clear tissue debris.

21. The method of claim 17 wherein the fluid-filled medium possesses a first electrical conductivity and wherein the injected fluid includes a second electrical conductivity.

22. The method of claim 21 wherein the first electrical conductivity substantially matches the second electrical conductivity.

23. The method of claim 21 wherein the fluid-filled medium and the injected fluid are electrically conductive fluids.

24. The method of claim 15 wherein the tube includes a cylindrical tube having a circular end face and wherein actuation of the RF generator generates a high temperature zone having a circular cross section for vaporizing a circular area of the tissue.

25. The method of claim 24 including the further step of sequentially indexing the tube end face after each actuation of the RF generator to cut a line in the tissue.

26. The method of claim 15 including the further step of controlling the length of time that the RF generator is actuated to control the amount of tissue vaporized.

* * * * *